United States Patent [19]

Collen

[11] Patent Number: 5,174,994
[45] Date of Patent: Dec. 29, 1992

[54] PHARMACEUTICAL COMPOSITION HAVING THROMBOLYTIC ACTIVITY

[75] Inventor: Désiré J. Collen, Winksele-Herent, Belgium

[73] Assignee: Leuven Research & Development VZW, Leuven, Belgium

[21] Appl. No.: 384,117

[22] Filed: Jul. 21, 1989

Related U.S. Application Data

[63] Continuation of Ser. No. 929,388, Nov. 10, 1986, abandoned.

[30] Foreign Application Priority Data

Nov. 11, 1985 [NL] Netherlands ................ 8503097

[51] Int. Cl.⁵ ............ A61K 37/62; A61K 37/547; A61K 37/54
[52] U.S. Cl. ................ 424/94.2; 424/94.64; 424/94.63; 514/822
[58] Field of Search .......... 424/94.63, 94.64, 94.2; 514/822

[56] References Cited

U.S. PATENT DOCUMENTS 3,555,000  1/1971  Wagner ........................ 424/101
4,285,932  8/1981  Smith ........................... 424/94.64

OTHER PUBLICATIONS

Zamarron et al., Thromb Haemostas, 52(1), 19-23 (1984).
Collen et al., Cited in Chem. Abstracts vol. 105:164686r (1986).
Collen et al., J. Pharmacol. Exp. Therap. vol. 231, No. 1 (1984) pp. 146-152.
Lijnen et al., Cited in Chem. Abstracts vol. 101:204095y (1984).
Zamarron et al., Cited in Chem. Abstracts vol. 101:204094x (1984).
Matsuo et al., Cited in Chem. Abstracts vol. 97:66201a (1982).

Primary Examiner—Jacqueline Stone
Attorney, Agent, or Firm—Armstrong & Kubovcik

[57] ABSTRACT

Plasminogen activators of the tissue-type and plasminogen activators of the urokinase-type appear to have a synergistic action in vivo when administered together as thrombolytic agents. Use in pharmaceutical compositions and in methods for the preparation and use thereof are set forth.

4 Claims, No Drawings

PHARMACEUTICAL COMPOSITION HAVING THROMBOLYTIC ACTIVITY

This application is a continuation of application Ser. No. 929,388 filed Nov. 10, 1986.

This invention relates to a thrombolytically active pharmaceutical composition which comprises a synergistic combination of known thrombolytic agents, as well as to the preparation and use of such a composition.

It is known that certain enzymes, called plasminogen activators, are capable of exerting a thrombolytic activity in vivo after intravenous administration to man or animal. Their activity is based upon activation of plasminogen, a blood constituent, which in its turn initiates a chain of reactions finally resulting dissolution (lysis) of a fibrin-containing blood clot when such clot is present in a blood vessel. The total activation mechanism is rather complex and may shown many differences depending on the type of plasminogen activator which has been used.

A distinction should be made between two types of plasminogen activator, viz. a tissue-type plasminogen activator (t-PA) and a urokinase-type plasminogen activator (u-PA). With regard to the latter one, a further distinction can be made between a two-chain form (referred to as urokinase) and a single-chain form (referred to as scu-PA). The activity mechanisms of these three plasminogen activators are different.

A plasminogen activator of the tissue-type (t-PA) is capable of causing plasminogen activation, but nearly exclusively in the presence of fibrin. This means that activation mainly occurs in the vicinity of a blood clot which is dissolved thereby, whilst virtually no activation of plasminogen occurs in the circulating blood. Such a plasminogen activator does not react with antisera against plasminogen activators of the urokinase-type.

The two-chain form of u-PA (referred to as urokinase) induces an efficient activation of plasminogen in blood, both in the presence and in the absence of fibrin. This means that blood clots can be dissolved but also that an activation of the fibrinolytic system in the circulating blood will occur which leads to fibrinogen break down and a bleeding tendency.

The single-chain form of u-PA (referred to as scu-PA) will activate plasminogen efficiently but only in the presence of fibrin-containing blood clots. Similar to t-PA, no activation of the fibrinolytic system in the circulating blood will occur notwithstanding the fact that the activation mechanisms are different and that scu-PA is immunologically unrelated to t-PA.

Among these three plasminogen activators, urokinase has been used in medical practice already for a long time and the described side effects have been felt to be a handicap therein. The other two plasminogen activators are still in the stage of clinical experimentation although such experimentation is relatively far advanced in the case of t-PA.

During further research, it has now been found that t-PA and scu-PA and also t-PA and urokinase have a synergistic effect in vivo i.e. a higher thrombolytic activity than the activity of the agents separately, when they are simultaneously administered to man or animal. This implies that an equivalent or larger thrombolytic activity can be obtained with smaller doses than previously used, thus resulting into savings of expensive agents. Moreover, this implies that the side effects which mainly occur with urokinase (activation of the fibrinolytic system in blood and breakdown of fibrinogen) may largely or completely be avoided.

The invention is based upon these findings. In one aspect, it provides a thrombolytically active pharmaceutical composition comprising a synergistic combination of tissue-type plasminogen activator (t-PA) and a urokinase-type plasminogen activator (u-PA) as an active ingredient. Such combination may be either a combination of t-PA with scu-PA or a combination of t-PA with urokinase.

In another aspect, the invention provides a method of preparing a thrombolytically active pharmaceutical composition, comprising the step of combining a tissue-type plasminogen activator (t-PA) with a urokinase-type plasmninogen activator (u-PA) in a pharmaceutically acceptable excipient or excipients. The resulting composition may have any appropriate form but is preferably in the form of an intravenous infusion fluid or a combination of such infusion fluids.

The tissue-type plasminogen activator to be used may be any conventional kind of t-PA, obtained from any suitable source. In the experiments to be described, the t-PA employed was recovered from the conditioned medium of a melanoma cell line, but recombinant t-PA, derived from transformed bacteria or cells will also be adequate.

The urokinase to be used is normally obtained from urine and will be commercially available.

The scu-PA to be used can in principle be obtained from several sources such as tissue cultures, urine, plasma and the like, but preferably it is recovered from the culture medium of conditioned cell cultures or transformed bacteria.

Several methods are available for isolation and purification of the plasminogen activators from their media. Such methods usually involve chromatography in many steps.

The two types of plasminogen activator (t-PA and u-PA) may be combined in any suitable way. Although it is possible to provide the combination as a two-component system, it is preferable to produce a one-component system in which both plasminogen activators are combined with each other in a common excipient. The excipient may be any medium which is conventional or suitable for this purpose.

The weight ratio between t-PA and u-PA in the invented composition may vary widely, for example in general between 1:10 and 10:1. A weight ratio between 1:2 and 2:1 is preferably used.

Pharmaceutical compositions containing a combination of plasminogen activators may have any form suitable for administration to man or animal. It is preferred, however, to have such compositions in the form of an intravenous infusion fluid or a combination of infusion fluids since this form offers the best chances for good results. Such infusion fluids or other composition forms may contain for instance about 0.2 mg/ml of plasminogen activator although in general concentrations ranging from 0.05 mg/ml to 10 mg/ml may be possible. Further, compositions having a higher concentration of plasminogen activator up to 100% may be made available provided that they are diluted to the just-mentioned range before utilisation.

The doses of t-PA and u-PA to be used when administering the pharmaceutical composition to a thrombosis patient may be significantly lower than required for each agent separately, due to the synergistic action of both agents. In general, such doses will be 5-30% and preferably 10-20% of the effective dose of t-PA and u-PA when used separately. The invention is illustrated by the following experiments which should not be interpreted to restrict the invention.

EXPERIMENT I

This experiment demonstrates the effect of several plasminogen activators and combinations thereof on an experimental thrombus produced in rabbits.

In anesthesized white rabbits (New Zealand type) weighing 2.4±3.0 kg, the external jugular vein was dissected over a length of 4 cm. A segment of the vein was isolated with the use of vascular clamps and its volume was determined. 0.1 ml thrombin solution (100 NIH-units per ml) was introduced into the emptied segment and followed by fresh blood mixed with 10-20 ul human fibrinogen labeled with radioactive iodine. The amount of blood corresponded to the predetermined volume of the vessel segment. A blood clot which formed in the vessel was allowed to age for 30 min before the vascular clamps were removed. Then, the amount of radioactivity in the vessel segment was determined.

Thereupon, several thrombolytic agents, namely t-PA, urokinase, scu-PA and combinations thereof were administered to the rabbits by infusion via a marginal ear vein. To this end, adequate amounts of the agents were diluted with a physiological saline solution to a final volume of 20 ml. The infusions continued over a period of 4 hours. 30 minutes thereafter, the vessel segment containing the thrombus was sutured at both ends and removed, whereupon the remaining radioactivity was determined. The degree of thrombolysis was calculated as the percent difference between the original radioactivity and the remaining radioactivity in the blood vessel segment.

A isotope balance was made by adding the radioactivity in the removed vessel segment and the radioactivity in the circulating blood at the end of the experiment and expressing the resulting value in percent of the originial radioactivity in the vessel segment. Radioactivity in the thyroid and in the lungs was negligible.

During the infusion of the thrombolytic agents, and also before and after that period, several blood samples were taken for measurement of radioactivity, fibrinogen content, d$_2$-antiplasmin content and the content of t-PA and scu-PA.

For more details on the experimental model, refer to D. Collen et al., J. Clin.Invest. 73, (1983), 368-376. The t-PA used in these experiments was obtained from the conditioned cell culture medium of a melanoma cell line, as described by D. C. Rijken et al., J.Biol.Chem., 256 (1981), 7035-7041 and D. Collen et al., Thromb.Haemost. 48, (1982), 294-296. Urokinase was from a commercial source and scu-PA was obtained from the conditioned medium of a lung adenocarcinoma cell line as described by D. C. Stump et al., Thromb. Heamost. 54 (1985), 122.

The results of this experiment are illustrated in table 1 in which the reported values represent the mean of three tests. In the control groups, receiving solvents only, the mean extent of thrombolysis was 9±1%.

From the table, it appears that thrombolysis was effected by systemic infusion of t-PA, urokinase or scu-PA and that the extent thereof was dose-dependent. Further, it appears that administration of urokinase in thrombolytic dose is associated with extensive fibrinogen breakdown.

Simultaneous administration of t-PA and scu-PA caused a comparable degree of thrombolysis at much lower doses. Simultaneous administration of t-PA and urokinase also had a synergistic effect on thrombolysis, but no synergism was observed between urokinase and scu-PA. None of the combined infusions induced systemic fibrinogen breakdown.

This indicates that a clear synergistic effect with regard to thrombolysis in vivo exists between t-PA and scu-PA and also between t-PA and urokinase. Combinations of these agents in doses of only 10-20% of the thrombolytic doses of each agent separately induce already an equivalent or larger thrombolytic effect. Synergism was observed in weight ratios of t-PA to u-PA between 1:10 and 10:1 and was most significant at weight ratios between 1:2 and 2:1.

TABLE 1

| Dose (mg/kg) | | | Thrombolysis (%) | Isotope recovery (%) | Fibrinogen level (%) |
| --- | --- | --- | --- | --- | --- |
| t-PA | scu-PA | Urokinase | | | |
| 0 | 0 | 0 | 9 ± 1 | 99 ± 3 | 92 ± 11 |
| 0.05 | 0 | 0 | 14 ± 1 | 97 ± 2 | 113 ± 5 |
| 0.125 | 0 | 0 | 24 ± 1 | 89 ± 1 | 105 ± 1 |
| 0.25 | 0 | 0 | 32 ± 1 | 89 ± 2 | 93 ± 1 |
| 0.50 | 0 | 0 | 57 ± 6 | 83 ± 1 | 101 ± 3 |
| 0 | 0.20 | 0 | 13 ± 1 | 94 ± 1 | 92 ± 12 |
| 0 | 0.50 | 0 | 21 ± 1 | 94 ± 3 | 97 ± 3 |
| 0 | 1.0 | 0 | 31 ± 1 | 90 ± 1 | 92 ± 2 |
| 0 | 0 | 0.2 | 12 ± 1 | 99 ± 2 | 101 ± 5 |
| 0 | 0 | 0.5 | 15 ± 2 | 94 ± 2 | 95 ± 5 |
| 0 | 0 | 1.0 | 23 ± 1 | 95 ± 1 | 91 ± 7 |
| 0 | 0 | 2.0 | 44 ± 3 | 98 ± 5 | 37 ± 26 |
| 0.025 | 0.05 | 0 | 15 ± 1 | 97 ± 1 | 101 ± 2 |
| 0.05 | 0.10 | 0 | 23 ± 1 | 96 ± 4 | 99 ± 3 |
| 0.1 | 0.2 | 0 | 51 ± 10 | 88 ± 4 | 106 ± 1 |
| 0.025 | 0 | 0.1 | 17 ± 2 | 94 ± 3 | 96 ± 5 |
| 0.05 | 0 | 0.2 | 27 ± 2 | 90 ± 2 | 100 ± 4 |
| 0.10 | 0 | 0.4 | 39 ± 7 | 93 ± 1 | 102 ± 1 |
| 0 | 0.05 | 0.1 | 11 ± 2 | 95 ± 1 | 88 ± 14 |
| 0 | 0.1 | 0.2 | 17 ± 2 | 93 ± 1 | 99 ± 8 |
| 0 | 0.2 | 0.4 | 25 ± 2 | 92 ± 1 | 102 ± 2 |
| 0.012 | 0.10 | 0 | 18 ± 2 | 98 ± 2 | 100 ± 1 |
| 0.050 | 0.025 | 0 | 28 ± 2 | 98 ± 1 | 92 ± 3 |
| 0.10 | 0.025 | 0 | 27 ± 2 | 90 ± 2 | 81 ± 4 |
| 0.012 | 0.20 | 0 | 24 ± 1 | 94 ± 1 | 99 ± 6 |
| 0.025 | 0 | 0.20 | 29 ± 3 | 96 ± 1 | 98 ± 1 |
| 0.038 | 0 | 0.30 | 49 ± 7 | 93 ± 1 | 96 ± 9 |
| 0.050 | 0 | 0.10 | 25 ± 7 | 94 ± 3 | 106 ± 5 |

EXPERIMENT II

This experiment demonstrates the thrombolytic effect of synergistic combinations of plasminogen activators in human patients with acute myocardial infarction and coronary artery occlusion.

In all patients, selective right and left coronary arteriography was performed from the right brachial artery. Then, a combination of t-PA and u-PA (scu-PA or urokinase) diluted with physiological saline to a final volume of 100 ml was administered by intravenous infusion over a period of 60 min. Arteriograhy of the occluded coronary artery was repeated at 15 min intervals or when signs of reperfusion occurred. Blood samples were collected on citrate and fibrinogen was assayed immediately therein. The results are collected in table 2 wherein the headings of columns 3 and 4 have the following meanings:

time (1): time interval between on set of symptoms and start of the infusion, time (2): time interval from start of infusion to reperfusion.

Reperfusion is defined as a complete filling of the coronary vessel distal to the original occlusion within a period of 3 cardiac cycles.

In a first study, a combination of 10 mg t-PA and 300,000 IU urokinase was administered to four patients with acute coronary occlusion (table 2A). In three of the four patients, reperfusion was obtained after 46, 50 and 53 minutes respectively. The fourth patient did not respond to this infusion and was also resistant to intracoronary streptokinase. None of the patients had any complications related to the infusion. The combined administration of t-PA and urokinase did not induce a systemic lytic state in any of the patients as evidenced by the unchanged levels of fibrinogen.

In a second study, a combination of 10 mg t-PA and 10 mg scu-PA was administered intravenously over one hour to seven patients having acute coronary occlusion (table B). A stable coronary reperfusion was obtained in five patients and a transient reperfusion in one patient (no. 4) whilst the remaining patient (no. 5) did not respond to the infusion. The combined infusion also did not induce fibrinogen breakdown here.

It may be concluded from table 2 that a combined administration of t-PA and u-PA to human patients will induce an efficient degree of thrombolysis, at doses significantly lower than normally used for each of the agents alone.

TABLE 2

| Patient | Sex/Age | Time (1) (h) | Time (2) (min) | Fibrinogen level (%) |
|---|---|---|---|---|
| A. 10 mg t-PA and 300,000 IU urokinase | | | | |
| 1 | M/64 | 4.5 | none | 100 |
| 2 | M/63 | 4.0 | 50 | 100 |
| 3 | F/62 | 3.7 | 46 | 100 |

TABLE 2-continued

| Patient | Sex/Age | Time (1) (h) | Time (2) (min) | Fibrinogen level (%) |
|---|---|---|---|---|
| 4 | M/69 | 4.6 | 53 | 100 |
| B. 10 mg t-PA and 10 mg scu-PA | | | | |
| 1 | M/66 | 1.8 | 23 | 88 |
| 2 | M/60 | 5.6 | 30 | 94 |
| 3 | M/65 | 5.7 | 60 | 100 |
| 4 | M/69 | 2.4 | 24 | 108 |
| 5 | M/58 | 6.0 | none | 115 |
| 6 | M/70 | 3.0 | 60 | 92 |
| 7 | M/51 | 5.5 | 45 | 93 |

I claim:

1. A therapeutic composition comprising tissue plasminogen activator (t-PA) and a urokinase plasminogen activator in single-chain form wherein said t-PA and urokinase plasminogen activator in single-chain form each is present per unit dose in said composition in an amount which results in a synergistic fibrin clot lysing interaction when said therapeutic composition is administered to a mammal having a fibrin clot to be lysed.

2. A therapeutic composition comprising tissue plasminogen activator (t-PA) and a urokinase plasminogen activator in two-chain form, wherein said t-PA and urokinase plasminogen activator in two-chain form each is present per unit dose in said composition in an amount which results in a synergistic fibrin clot lysing interaction when said therapeutic composition is administered to a mammal having a fibrin clot to be lysed.

3. A method for the treatment of thromboses comprising administering to a mammal in need thereof a pharmaceutical composition according to claim 1 in an amount which results in a synergistic fibrin clot lysing interaction.

4. A method for the treatment of thromboses comprising administering to a mammal in need thereof a pharmaceutical composition according to claim 2 in an amount which results in a synergistic fibrin clot lysing interaction.

* * * * *